US008747325B2

(12) United States Patent
Bacal et al.

(10) Patent No.: US 8,747,325 B2
(45) Date of Patent: Jun. 10, 2014

(54) NON-INVASIVE METHOD FOR DIAGNOSING THE SEVERITY OF HEART FAILURE BY EXTRACTING AND ANALYZING ACETONE CONCENTRATIONS IN CAPTURED EXHALED BREATH

(75) Inventors: Fernando Bacal, São Paulo SP (BR); Fabiana Goulart Marcondes Braga, São José dos Campos SP (BR); Ivano Gebhardt Rolf Gutz, São Paulo SP (BR); Guilherme Lopes Batista, São Paulo SP (BR)

(73) Assignees: Fundacao de Amparo A Pesquisa Do Estado De Sao Paulo (FAPESP) (BR); Universidade De Sao Paulo (USP) (BR)

( * ) Notice: Subject to any disclaimer, the term of this patent is extended or adjusted under 35 U.S.C. 154(b) by 713 days.

(21) Appl. No.: 12/838,204

(22) Filed: Jul. 16, 2010

(65) Prior Publication Data

US 2012/0011918 A1    Jan. 19, 2012

(51) Int. Cl.
*A61B 5/08*    (2006.01)

(52) U.S. Cl.
USPC ........... 600/484; 600/529; 600/532; 600/540; 600/543

(58) Field of Classification Search
USPC .......................... 600/484, 529–543; 73/23.35
See application file for complete search history.

(56) References Cited

U.S. PATENT DOCUMENTS

| 4,114,422 | A | * | 9/1978 | Hutson | 436/130 |
| 4,587,834 | A | * | 5/1986 | Fisher | 73/23.35 |
| 5,573,005 | A | * | 11/1996 | Ueda et al. | 600/543 |
| 5,992,214 | A | * | 11/1999 | Schlitt | 73/23.35 |
| 6,763,704 | B2 | * | 7/2004 | Bowe, Jr. | 73/53.01 |
| 7,992,422 | B2 | * | 8/2011 | Leddy et al. | 73/23.3 |
| 2003/0208133 | A1 | * | 11/2003 | Mault | 600/532 |
| 2004/0162500 | A1 | * | 8/2004 | Kline | 600/532 |
| 2007/0232952 | A1 | * | 10/2007 | Baddour | 600/543 |
| 2008/0004542 | A1 | * | 1/2008 | Allen et al. | 600/532 |

(Continued)

FOREIGN PATENT DOCUMENTS

| WO | WO97-38307 A1 | 10/1997 |
| WO | WO97-39367 A1 | 10/1997 |

(Continued)

OTHER PUBLICATIONS

Wang et al., "Breath Analysis Using Laser Spectroscopic Techniques: Breath Biomarkers, Spectral Fingerprints, and Detection Limits", 2009, vol. 9, p. 8230-8262.*

(Continued)

*Primary Examiner* — Jacqueline Cheng
*Assistant Examiner* — Puya Agahi
(74) *Attorney, Agent, or Firm* — Hayes Soloway P.C.

(57) ABSTRACT

The invention application presents a fast, efficient, reproductive alternative of a non-invasive method for diagnosing the severity of heart failure based on a specific biomarker. An additional object of the present invention is a collector device for the biomarker from exhaled breath that is portable, simple, low cost and does not need to run on electric power. This invention advantageously permits the replacement of invasive diagnosis methods, favoring the patient's comfort in addition to the agility and speed of medical attention at hospitals, and may become a standard method for all suspected cases of circulatory disease and heart failure and, more specifically, decompensated heart failure.

25 Claims, 7 Drawing Sheets

(56) References Cited

U.S. PATENT DOCUMENTS

| | | | |
|---|---|---|---|
| 2008/0009761 A1* | 1/2008 | Acker et al. | 600/532 |
| 2009/0163825 A1 | 6/2009 | Hirsh | |
| 2009/0275852 A1* | 11/2009 | Oki et al. | 600/532 |
| 2009/0281442 A1* | 11/2009 | Paz et al. | 600/532 |
| 2009/0290161 A1* | 11/2009 | Atkin et al. | 356/433 |
| 2010/0292601 A1* | 11/2010 | Dompeling et al. | 600/543 |

FOREIGN PATENT DOCUMENTS

| | | |
|---|---|---|
| WO | WO98-57145 A1 | 12/1998 |
| WO | WO00-36976 A1 | 6/2000 |
| WO | WO01-93743 A1 | 12/2001 |
| WO | WO2005-033707 A1 | 4/2004 |
| WO | WO2004-065404 A1 | 8/2004 |
| WO | WO2007-010425 A1 | 1/2007 |

OTHER PUBLICATIONS

Kupari et al., "Breath Acetone in Congestive Heart Failure", The American Journal of Cardiology, vol. 76, 1995.*

Anderson et al., "Measuring airway exchange of endogenous acetone using a single-exhalation breathing maneuver", 2005, Departments of Medicine and Physiology and Biophysics, University of Washington.*

Kang et al., Evaluation of the limit-of-detection capability of carbon black-polymer composite sensors for volatile breath biomarkers, 2010, Elsevier, pp. 55-60.*

Terence H. Risby, et al., "Clinical Application of Breath Biomarkers of Oxidative Stress Status", Free Radical Biology & Medicine, 1999, vol. 27, p. 1182-1192.

P.P. Rosias, et al., "Breath Condenser Coatings affect Measurement of Biomarkers in Exhaled Breath Condensate", Eur Respir J, 2006, vol. 28, No. 5, p. 1036-1041.

P.P. Rosias, et al., "Biomarker Reproducibility in Exhaled Breath Condensate Collected With Different Condensers", Eur Resp J, 2008, vol. 31, No. 5, p. 934-942.

"Cost Analysis of EcoScreen v. RTube", Respiratory Research, Inc., 2005.

Svante Berntsson, "Spectrophotometric Determination of Acetone by the Salicylaldehyde Method", Anal. Chem., 1956, vol. 28, No. 8, p. 1337.

Norio Teshima, et al., "Determination of Acetone in Breath", Analytica Chimica Acta 535, 2005, p. 189-199.

Rudolf Berger, et al., "B-Type Natriuretic Peptide Predicts Sudden Death in Patients with Chronic Heart Failure", Journal of the American Heart Association, Circulation 2002, p. 2392-2397.

Wolfram Miekisch, et al., "From Highly Sophisticated Analytical Techniques to Life-Saving Diagnostics: Technical Developments in Breath Analysis", Trends in Analytical Chemistry, vol. 25, No. 7, 2006, p. 665-673.

Chuji Wang, et al., "Breath Analysis Using Laser Spectroscopic Techniques: Breath Biomarkers, Spectral Fingerprints, and Detection Limits", Sensors, 2009, vol. 9, p. 8230-8262.

Cap, et al., "Selected Ion Flow Tube Mass Spectrometry of Exhaled Breath Condensate Headspace", Rapid Commun. Mass Spectrom, 2008, vol. 22, p. 2844-2850.

Mariell Jessup, et al., "2009 Focused Update: ACCF/AHA Guidelines for the Diagnosis and Management of Heart Failure in Adults", American Heart Association, Circulation 2009, 119, p. 1977-2016.

Kenneth Dickstein, et al., "ESC Guidelines for the Diagnosis and Treatment of Acute and Chronic Heart Failure 2008", European Heart Journal, 2008, 29, p. 2388-2442.

Takahiro Mitsui, et al., "Is Acetone a Normal Breath Constituent in Japanese?", Clinica Chimica Acta 280, 1999, p. 205-208.

Markku Kupari, et al., "Breath Acetone in Congestive Heart Failure", The American Journal of Cardiology, vol. 76, Nov. 15, 1995, p. 1076-1978.

T.A. McDonaugh, et al., "Biochemical Detection of Left-Ventricular Systolic Dysfunction", The Lancet, vol. 351, Jan. 1998, p. 9-13.

* cited by examiner

NON-INVASIVE METHOD FOR DIAGNOSING THE SEVERITY OF HEART FAILURE BY EXTRACTING AND ANALYZING ACETONE CONCENTRATIONS IN CAPTURED EXHALED BREATH

FIELD OF THE APPLICATION

This invention application presents a fast, effective and reproducible alternative of a non-invasive method for diagnosing the severity of heart failure based on a specific biomarker. An additional object of the present invention is a collector device of exhaled air, being portable, simple and low cost and does not need to run on electric power. This invention advantageously permits the replacement of invasive diagnosis methods, favoring the patient's comfort in addition to the agility and speed of medical attention at hospitals, and may become a standard method for all suspected cases of circulatory disease and heart failure and, more specifically, decompensated heart failure. According to data from the Brazilian Ministry of Health, diseases related to the circulatory apparatus occupy $3^{rd}$ place in hospitalizations. Among admissions, 28% of all hospitalizations for cardiovascular diseases are related to heart failure (DATASUS, 2004). In Europe there are at least 15 million patients with heart failure in 51 countries; the prevalence of heart failure is 2-3% and rises sharply at 75 years old (ESC Guidelines for the diagnosis and treatment of acute and chronic heart failure 2008, Eur. Heart Journal 2008). This information emphasizes that heart failure is a disease of wide repercussion both in number of attendances as in the amount of health resources destined for the evaluation, diagnosis and treatment thereof. In this context, methods of diagnosing diseases, preferably specific diseases, have major importance and the search for developing methods and devices that are simpler and less costly is necessary and competitive.

BACKGROUND OF THE INVENTION

Said technology has major field of application and a growing market. A study carried out in the USA shows that the largest direct costs with medical care are related to heart failure, estimated at 10 to 38 billion dollars per year (cited by Maisel et al., Rapid measurement of B-type natriuretic peptide in the emergency diagnosis of heart failure, The New England Journal of Medicine, v. 347, n. 3, p. 161, 2002). A complete study on heart failure in Brazil presented by Guideline on Heart Failure (HF) III in Brazil in 2009 and studies by DATASUS 2004 show the total expenditures by the Brazilian government to pay for all the hospitalizations and the position occupied by the diseases of the circulatory apparatus, $3^{rd}$ place in frequency, being supplanted only by childbirth/pregnancy/puerperium and by diseases of the respiratory apparatus (Albanesi, F. M., Heart failure (HF) in Brazil, Arq. Bras. Cardiol. vol. 71 n. 4, 1998). In 2004, in Brazil the number of total hospitalizations under the Public Health System—SUS (Brazilian Ministry of Health) was approximately 11.5 million, of which 340 thousand were admissions for heart failure, accounting for 28% of all hospitalizations for cardiovascular diseases and 3% of total causes. In 2007 the total number of hospitalizations was 11.3 million and approximately 295 thousand for heart failure. Although the number has fallen, the unit cost has increased about 20%. This information emphasizes that heart failure is a disease with wide repercussion both in number of attendances as in the amount of health resources destined for the evaluation, diagnosis and treatment thereof. In this context, diagnosis methods, preferably for specific diseases, have major importance, not least in relation to a shorter diagnosis time, more efficient treatment, implying in a reduced hospitalization time and lower cost for the event.

The main prognosis markers identified in chronic HF were cited by Brazilian Guideline III on Chronic Heart Failure and by AACF/AHA Guidelines for the Diagnosis and Management of Heart Failure in adults 2009, but no model uses all of them in a systematic way to stimulate survival. Some of them such as neurohormones (norepinephrine or endothelin) are not routinely used, because their measurements are complex, expensive and do not add any additional intervention in therapeutics. Another well accepted marker is B-type natriuretic peptide (BNP) which when remaining high during hospitalization is a predictor of worse prognosis, and may predict re-hospitalization and/or death of the individual. This biomarker will be described in more detail below. Because treatment of heart failure has improved over the past 10 years, the older prognostic models need to be revalidated and newer prognostic models may have to be developed (AACF/AHA Guidelines for the Diagnosis and Management of Heart Failure in adults 2009).

Some heart failure biomarkers known in the state of the art are presented below, but the currently existing methods and devices are not yet designed to evaluate the degree of decompensation of heart failure. Further, they are methods that involve blood collection and, therefore, are invasive. In light of existing technologies, as presented below, none of them brings together the advantages of the present proposal like non-invasiveness, simple and effortless sample collection and high sensitivity and selectivity for decompensated heart failure.

The B-type natriuretic peptide (BNP) is a polypeptide released by the ventricular myocytes in response to overload of volume, overload of pressure and increased parietal tension. Both its physiologically active form, the BNP, and its inactive bioproduct, the pro-BNP N-terminal can be reliably dosed. Studies cited by the Brazilian Cardiology Society (Arquivos Brasileiros de Cardiologia, Volume 92, 6, 1, 2009) have demonstrated the important use of the BNP biomarker in the evaluation of patients with suspected HF diagnosis in the emergency room and at outpatient level. In these circumstances, the BNP is particularly useful in eliminating the diagnosis of HF, by its high negative prediction value. The BNP is influenced by various factors (age, BMI—body mass index, renal function) which may interfere in its diagnosis accuracy and require specific cut points. Additionally, the BNP may be high in the absence of HF in conditions such as systemic arterial hypertension, valvulopathies, myocardial ischemia, left-ventricular hypertrophy (LVH) and pulmonary embolism. The use of two cut points, one to "exclude" (high negative predicted value), the other to "confirm" (high positive predicted value) and an intermediary range, in which other diagnoses should be considered, have been recommended and may facilitate its clinical use. Various studies have demonstrated the correlation between the BNP levels and the severity of HF as well as the independent prognostic value of these biomarkers for total mortality, cardiovascular mortality and hospitalization both in acute HF and chronic HF. The prognostic importance of BNP was also demonstrated in chagasic cardiomyopathy. There is also recent evidence that the use of BNP to guide therapeutics may be associated to better clinical evolution and cost reduction, though this diagnosis and prognosis method using the biomarker BNP is invasive and requires blood samples from patients, as described by Berger et al (B-Type Natriuretic Peptide predicts Sudden Death in Patients with Chronic Heart Failure, *Journal of the American Heart Association*, p. 2392, 2002), differing from the present technology which presents a non-invasive method, wherein the results bear an accuracy equivalent to the BNP as biomarker, and also foresee the severity of heart failure by analyzing a sample obtained comfortably, in a non-invasive, fast and easy manner. Therefore, the present invention is an alternative with efficiency equivalent to the BNP biomarker and also has the advantage of not requiring blood collection. It is a more comfortable collection method and offers less risk for the patient.

Other works also involve the BNP biomarker for diagnosing diseases such as congestive heart failure in patients with dyspnea of undefined etiology. The dosage of this biomarker allows dyspnea of cardiac etiology to be differentiated from other causes (Maisel et al. Rapid measurement of B-type natriuretic peptide in the emergency diagnosis of heart failure, The New England Journal of Medicine, v. 347, n. 3, 2002; McDonagh et al. Biochemical Detection of the Left-Ventricular Systolic Dysfunction, The Lancet, v. 351, n. 3, 1998). The method proposed in this invention has a good correlation with the levels of BNP as demonstrated ahead, but differently to the BNP biomarker, it is a non-invasive method and could also be used as biomarker of this disease with the advantage of being easy to collect and non-invasive.

Early diagnosis of a certain disease in an individual is often important for the successful treatment of this disease. There is a wide variety of techniques to evaluate specific diseases according to the symptoms. It is possible to cite as an example the use of collection of urine and blood to detect metabolic alterations that reflect the diagnosis of a certain disease or decompensation thereof. Many of these techniques are invasive or uncomfortable for the patient. A non-invasive technique potentially for determining the presence of a wide variety of diseases affecting an individual is breath analysis. Over four hundred different chemical compounds can be detected in exhaled human breath. The presence of a given disease may be indicated by adding or changing the concentration of one or more components or the combination of both in the gaseous sample of exhaled air. These components are the biomarkers or biochemical markers. The detection of a biomarker has been a complex task due to the great number of constituents in exhaled air, great interpersonal variation in exhaled air composition and due to the constant alteration of the constituents as a result of environmental pollutants.

A non-invasive analysis of breath has the potential to replace blood and urine analysis for many compounds, especially the volatile organic compounds of the metabolism, released by the capillary blood vessel in the pulmonary alveoli and determinable in the exhaled air. Despite the low concentration of exhaled compounds, advances in analytical chemistry in the last decades allowed the quantification of many of them, opening the possibility to apply such information in toxicology and especially for diagnosing diseases.

Collection devices for exhaled air based on condensation, adsorption on a solid or liquid phase as well as other devices will be presented in the background to the present invention and the advance thereof in relation to the state of the art. Among these devices, an adsorbent selected was dimethylsilicone, considered to have characteristics similar to the pulmonary alveoli. The efficiency and sensitivity of a collection device for exhaled air condensate are fundamental characteristics for analyzing the trace compounds to the easily detectable concentrations, but the major advantage of a device consists of the guarantee of an accurate subsequent quantitative analysis in order to assure correlations with diseases and render it a suitable tool for the method of diagnosing diseases. Studies such as those by Miekisch and Schubert in 2006 (Trends in Analytical Chemistry, v. 25, No. 7, 2006), Wang and Sahay in 2009 (Sensors v. 9, p. 8230-8262, 2009), Mitsui et al., 1999 (Clinica Chimica Acta 280 (1999) p. 205-208) and Risby and Sehnert in 1999 (Free Radical Biology & Medicine, v. 27, Nos. 11/12, p. 1182-1192, 1999) are teachings present in the state of the art.

Although the American Society of Thoracic Surgery and other associations have published on exhaled air condensate, in general the methodological recommendations for collecting and analyzing exhaled air condensate, there are still certain methodological obstacles to be overcome, such as the use of various systems as non-standardized collector devices (cited by Rosias and col. Biomarker reproducibility in exhaled breath condensate collected with different condensers. Eur. Resp. J. 31, p. 934-942, 2008).

Optimal collector devices, detection of ideal biomarker and EBC measurement are reciprocal pre-requirements for any normalization. However, current condensation systems present efficiency below that considered optimal, with reduced measurability and relative loss of non-condensated exhaled air, which reflects in variable volumes having low biomarker reproducibility (Rosias et al. Exhaled breath condensate in children: pearls and pitfalls. Pediatr Allergy Immunol; 15, p. 4-19, 2004). Logically, the change by means of guided flows of the breath air promotes the increase of the condensation surface, and recovery of the condensate may improve condensation. Additionally, the current projects have different internal coatings and, therefore adhesives with different interactions with exhalation markers. Recently, a loss of biomarkers from the sampling within the system was demonstrated, both in vitro and in vivo, for 8-isoprostane and albumin, to the detriment of condenser systems not made of glass, and in favor of glass and silicone condensers.

Faced with the need to improve and develop non-invasive diagnosis methods for classes of diseases or for specific diseases, the latter being the objective of said invention, the matter of biomarkers and the state of the art of the collective sampling devices for exhaled air will be addressed to substantiate the subject and demonstrate the technical specificity and the commercial interest for the object of the present invention.

The acetone detected through the exhaled air has been presented in literature as a marker of possible diseases such as, for example, in sufferers of Diabetes Mellitus and Pulmonary Disease. However, on many occasions it is not considered a suitable indicator, as set forth ahead. The originality of the present invention comprises a non-invasive diagnosis method of heart failure and its severity through the sampling of exhaled air of patients followed by a quantitative determination of acetone.

Since acetone in the human breath is a promising diagnosis method and seems to be an important marker for noninvasive diagnosis of decompensated diabetes, novel chemoresistive detectors and acetone sensors are being developed and should allow rapid measurement of low acetone concentrations. However, all the studies involve patients with diabetes and no one with heart failure. This diagnosis method was not designed to diagnose the degree of heart failure decompensation. The present invention comprises a noninvasive method, a new biomarker to diagnose and determine the severity of heart failure.

As a way of exemplifying the particularity of acetone as a biomarker, we cite the study presented by Studer et al., 2001 (The Journal of Heart and Lung Transplantation, v 20, Issue 11, 2001, p. 1158-1166) whose objective was to evaluate acetone as well as other possible biomarkers, as an indication of organ rejection in lung transplant patients with the aim of replacing the invasive diagnosis of biopsy for a non-invasive one. At the end of the study, it was concluded that acetone cannot be considered a biomarker for this case. The failure of studies such as this one shows that acetone is not an obvious biomarker for diseases.

Teshima et al., 2005 (Anal. Chim. Acta v. 535, 2005, p. 189-199) describe a complete analyzer comprising the sampling and the determination of acetone in a rather complex single system. The exhaled air is forced to flow around a polypropylene tube with porous walls. The acetone crosses through the membrane pores by diffusion, becoming dissolved in the collector liquid in the tube. In contact with salicylaldehyde and under heat, the acetone reacts to form a colored compound that is photometrically quantified using an LED (light emitting diode) as radiation source, a Teflon tube as long-path optical cell and a photodiode as detector. The patient can breathe into a mask directly coupled to the system, or breathe into a heated balloon, from which the sample is slowly transferred to the measuring system. The system is rather complex and expensive, requiring electrical power for the solenoid valves, air pumps and for heating the balloon. Differently, in the present invention proposal, the collector device presented is simple, sensitive and portable and the analysis of the sample collected can be carried out, just after sampling or at a later time by conventional chromatographic, spectrophotometric or other methods, commonly used in analytical laboratories. The sample can be frozen, for long-term stability. Besides the differences in relation to the device, the study of Teshima et al., does not demonstrate and does not indicate the specific application of the device for diagnosing a specific disease.

The study presented by Cap et al., 2008 (Rapid Communications in Mass Spectrometry, 2008, 22, p. 2844-2850) involves the collection of exhaled air condensate from patients suffering from pulmonary diseases, in order to evaluate potential pulmonary inflammation biomarkers. This study comparatively used a commercial collector device EcoScreen (Jaeger, Germany) and a system developed by the authors comprising a mouthpiece linked directly to a cooling fluid from which a sample was collected for 10 minutes and during exhalation the nose was kept obstructed, besides containing a headspace at the output of the collector to capture the volatile compounds. Said commercial device EcoScreen, according to information from the manufacturer, is suitable for the following markers: hydrogen peroxide, ammonium nitrate/nitrite, chloride, substances reactive to thiobarbituric acid (TBARS), metabolites of arachidonic acid (eicosanoids), leukotriene B4 that is, leukotrienes C4, D4, E4, prostaglandin E2, isoprostane, markers of protein, interleukin (for example IL-2, IL-6, IL-8), catecholamines, etc. The commercial device presents nothing on collecting and detecting acetone. The object of the present invention compares advantageously with the EcoScreen device not only because it contains simpler and less costly elements, but also does not need to run on electric power, being suitable for situations in which portability is required without depending on electricity, obviously involving lower investment costs.

The study carried out by Rosias et al., 2006 (Breath condenser coatings affect measurement of biomarkers in exhaled breath condensate, European Respiratory Journal, v. 28, p. 1036, 2006) compares different types of condenser coatings in devices for capturing exhaled air from breath. In this study, it was concluded that the type of coating influences the biomarker measurement. The types of condenser coatings analyzed were: silicone, glass, aluminum, polypropylene and teflon, also compared with the commercial device EcoScreen cited previously. It was possible to note that according to the biomarker, a type of coating is desirable in order to make it more suitable for the reading thereof. A silicone or glass-coated condenser is more efficient for reading a biomarker 8-isoprostane or albumin than EcoScreen, aluminum, polypropylene or Teflon. Another sophisticated commercial device for collecting exhaled air condensate is cited in the study as RTube (Respiratory Research Inc., Charlottesville, Va., USA). This study demonstrates that the construction of a device for collecting exhaled air condensate for non-invasive prognosis, although having been presented in literature for application to certain diseases and some markers, is not obvious, because compared to different biomarkers and different diseases, there are specificities that must be considered for the reliable biomarker sampling and subsequent determination. The biomarkers sought in the study are for pulmonary diseases and inflammations of the airways and not for decompensated heart failure, as in the. The device for collecting the biomarker acetone from exhaled air in the present invention involves extraction by dissolution in a liquid phase and the factors that influence the efficiency of the collection are described. These factors allow greater contact, mixture and increased solubility of the biomarker, to attain greater sensitivity of the non-invasive diagnosis method.

The study carried out by Rosias et al. in 2008 (Biomarker reproducibility in exhaled breath condensate collected with different condensers, European Respiratory Journal, v. 31, p. 934, 2008) evaluated the reproducibility of the volume of exhaled breath condensate for some types of condensers (glass, silicone, commercial EcoScreen) including a new device developed by the authors (optimized glass condenser). This study evaluated 3 biomarkers: hydrogen peroxide, 8-isoprostane and cytokine and, therefore, the possibility of acetone as biomarker was not the target of the study. It was concluded that the proposed condenser presents efficiency similar to the commercial device EcoScreen and significantly better compared to the silicone and glass condenser. It was demonstrated through collecting exhaled air condensate by the device proposed that the concentration of the biomarker 8-isoprostane was significantly greater than the concentration in the samples collected by the other devices, and this was not observed with the other biomarkers hydrogen peroxide and cytokine.

International patent application WO2004-065404 A1 of Jan. 16, 2003 discloses the use of biosensors for diagnosing and treating disease both through samples of exhaled air and blood samples. The biosensors include chains of RNA nucleotides or aptamer in combination with nanotechnology to promote an effective and efficient method for diagnosing a condition or a disease. The method for detecting the biomarker in exhaled breath comprises exposure of exhaled breath air to an aptamer (oligonucleotide or peptide molecule which is linked to a specific target molecule) capable of selectively linking to a biomarker with a photo-signaling molecule and consequent detection of the signal generated by the photo-signaling molecule such as, for example, a fluorescent polymer. Another object of the technology comprises an analysis of bodily fluids and, therefore, differs from said proposal. Hence, although the technology cites acetone among the selected biomarkers, the technology is entirely different to the present invention, as is its application.

International patent application WO2005-033707 A1 of Oct. 2, 2003 discloses systems and methods for the ex-vivo diagnosis analysis of samples of bodily fluids, including exhaled breath and blood. The present invention uses nanostructure-based assemblies in combination with a sensor technology to provide an efficient and accurate means for identifying the presence of markers or biomarkers in a sample of bodily fluid. In a preferred embodiment, the nanostructure-based assemblies include detecting means such as RNA oligonucleotide chains or aptamers and markers such as DMSO. This international patent application cites an example of diagnosing traumatic brain injury, acute and chronic neurological diseases and disorders (for example, Alzheimer, Parkinson) and other clinical conditions by the in vitro detection of biomarkers linked to oxidative stress. Besides neurological diseases, it presents an example of application for diagnosis of bronchogenic carcinoma, prostate cancer. The biomarkers used do not correspond to acetone.

Patent application US 2009-0163825A1 of Dec. 19, 2007 describes a device for medically managing patients with diabetes, more specifically an alarm/warning system for hypoglycemia and hyperglycemia. The biomarker used in the system proposed by this North American patent application is the acetone of exhaled breath, of which the relationship between acetone and diabetes has already been known for some time. This same patent application cites the relationship between acetone and pulmonary diseases. This application cites two patent applications related to the detection of acetone as an indicator of ketosis and weight loss via fat metabolism (US 2004-0236244 A1) and a patent application related to a sensor with enzyme coupled to a signal measurer to read the level of acetone and method of using the sensor for detecting disease and weight loss (US 2005-0084921 A1). There is no association of a non-invasive diagnosis method for decompensated heart failure from an acetone biomarker. This patent application does not cite the levels of acetone detected by the device. The state of the art reports that diabetic patients produce significantly high acetone levels, higher than those detected in patients with heart failure. The present invention is capable of detecting acetone in exhaled air condensate in low concentrations, in the order of 0.5 ug/L, this clearly being a diagnostic advantage.

Patent application WO0036976 A1 of Dec. 18, 1998 presents an alternative system for detecting exhaled breath, more specifically levels of NO and $CO_2$ or both.

International patent application WO2007-010425 A1 of Jul. 19, 2005, discloses a gas analyzer comprising a transistor that has a cavity and a semiconductor channel with a cavity between them where there is introduced the fluid sample and change of property generated between the contact of the fluid with the semiconductor, preferably polyarylamine and in response generates a signal indicating the concentration of the sample component. The samples may contain nitrogen monoxide, acetone, ethanol, carbon monoxide and isoprene, however, the embodiment example was presented only for nitrogen monoxide being, for example, capable of detecting low concentrations of nitrogen monoxide such as contents detected in patients with asthma (20 to 100 parts per billion, ppb). Therefore, in view of the information, it is not possible to evaluate and verify whether the device also presents a result or an efficient result when the marker is acetone.

Patent application WO1997-038307 A1 of Apr. 9, 1997 proposes methods of quantifying preferably carbon dioxide and nitric oxide but also encompasses other volatile and non-volatile compounds of exhaled breath such as oxygen, nitrogen, nitrogen dioxide, hydrogen peroxide, proteins, surfactants, DNA, acetone, ammonia, sulphurous compounds, acetylene, carbon monoxide, ethane and pentane. Besides this 1997 patent application failing to present embodiment examples of collection, detection and quantification of acetone in exhaled breath, the system is different and the method for determining the levels of the compound of interest is not the object of the present invention.

International patent application WO 1998-057145 A1 of Jun. 10, 1997 refers to the diagnosis of lung cancer, but without restrictions, and application for the following diseases is also cited: kidney failure, disease of the liver or diabetes through the analysis of exhaled breath air. Examples cited of biomarkers as strong indicators of lung disease are: ε-caprolactone, 2-butanone and acetone. Said patent application refers to a method of detecting a specific organic volatile compound as indicative of a biological condition when in a certain quantity making use of an electromagnetic radiation generator directed towards the sample, differently to the present invention which does not disclose a method of analyzing a sample of exhaled air.

International patent application WO2001-93743 A1 of Jun. 7, 2000, refers to the analysis of breath in mammals, particularly for detecting ketones in the exhaled breath of a person for monitoring exercises and diet, as well as for diagnosing insulin-dependent diabetes. In periods of low calorie intake, the contents of ketones and fatty acids increase. In the background to the invention, the application cites numerous patent applications relating to methods for detecting ketones and acetone, however, the present proposal differs from all by being an instrument for collecting, and not for analyzing a chemical composition and, therefore, a simple, fast, portable and low cost device which allows the sample to be analyzed by any method or equipment already known and accredited such as, for example, chromatographic and spectrophotometric analytic techniques and methods. The device presented in WO2001-93743 A1 is related to the emission of radiation, ultrasonic transducers and specific sensor. Said device to capture and analysis of the sample could be used for the non-invasive diagnosis method for heart failure proposed in this invention provided it is accurate and highly efficiency. The differentiating factor of the collection device proposed in this invention comprises a modifier, which increases the solubility of the acetone in relation to the air of the breath itself, meaning it is captured more efficiently and, therefore, favors the achievement of the suitable biomarker level in a fast collection time. This differential is highly important for a person suffering from decompensated heart failure. Prior studies have demonstrated that devices involving prolonged collection time may hinder, and even prevent patients with decompensated heart failure from undergoing an examination. This occurs because in this condition the patients suffer from tachypnea and/or dyspnea, that is, an increased number of respiratory cycles per minute, related to respiratory discomfort secondary to decompensation of chronic disease.

International patent application WO2003-039367 A1 of Nov. 9, 2001 refers to a hand apparatus for detecting a pre-defined component in the breath capable of capturing the signal of the component in a certain time. The signal of the breath component must be related to an indicator of fat metabolism. More specifically to analyze acetone in exhaled breath through an enzymatic biosensor specific for acetone. The device of this patent application comprises a collector, breath sample input, a sensor, more specifically an electrochemical biosensor to detect a pre-determined breath component that produces a signal at a certain time, an electric circuit to communicate with said sensor that reads said signal of the breath component, wherein the magnitude of the signal is based on the concentration of said component of the sample, an electric-digital converter, a microprocessor for processing the digital signal for use as an indicator of the fat metabolism and a communication display of the microprocessor data as indicator of the fat metabolism. The diagnosis method and device proposed here are both different to the application proposed by said international patent application.

A study presented by Kupari et al. (The American Journal of Cardiology, 76, 1076 p., 1995) does not relate the biomarker to the severity of heart failure, one of the major differentiating factors of the present invention, conferring the method an application and an interest that better suits the needs of hospitals, serving as parameter as whether or not to hospitalize the patients arriving at the attendance centers. It is therefore a major challenge to develop a device with high sensitivity and a non-invasive method of diagnosing the severity of heart failure.

Hence, there is a major need to develop an accurate and efficient system for collecting volatile compounds present in exhaled breath, in which one or more compounds called biomarkers are indicators of a certain disease. It is therefore a major challenge to relate a compound present in exhaled breath to a specific disease and associate it to the diagnosis of a disease in light of the change in its concentration levels.

BRIEF DESCRIPTION

A non-invasive method for diagnosing heart failure characterized by comprising:

(a) analysis of acetone in the exhaled air as a biomarker of heart failure wherein the detection and quantification of the acetone can be made by any suitable technique for direct analysis or after sample collection, which may be selected from a group comprising, but not limited to: chromatography, mass spectrometry, infra-red or ultra-violet-visible spectrophotometry, gas sensors and electronic noses;
  (b) indication of the severity of heart failure in accordance with the following ranges:
    (b1) acetone concentration with a preferable upper limit of 0.85 mcg/L indicates that the patient does not have a heart failure condition;
    (b2) acetone concentration with preferable lower and upper limits of 0.85 up to 2.6 mcg/L indicates compensated heart failure;
    (b3) acetone concentration with a preferable lower limit of 2.6 mcg/L indicates decompensated heart failure (heart failure with congestion and/or heart failure with low output).

An additional object of the present invention is a non-invasive method of prognosticating heart failure characterized by comprising:
  (a) collection of a sample of exhaled air in a device that extracts one or more biomarkers from gaseous phase to a liquid phase comprising pure water, organic substances with high acetone affinity, chemical reagents or mixtures of substances that increase the retention efficiency of the biomarker of interest.
  (b) detection and quantification of the acetone biomarker in the sample of the exhaled air wherein the analytical technique can be selected from a group comprising, but not limited to: chromatography, mass spectrometry, infra-red or ultra-violet-visible spectrophotometry, gas sensors and electronic noses; and
  (c) indication of the prognosis of the patient suffering from decompensated heart failure comprising the following ranges:
    (c1) Acetone concentration less than 0.85 mcg/L indicate that the patient does not have a heart failure condition;
    (c2) Acetone concentration between 0.85 and 2.6 mcg/L indicate compensated heart failure;
    (c3) Acetone concentration higher than 2.6 mcg/L indicate decompensated heart failure (heart failure with congestion and/or heart failure with low output).

Figure 9:
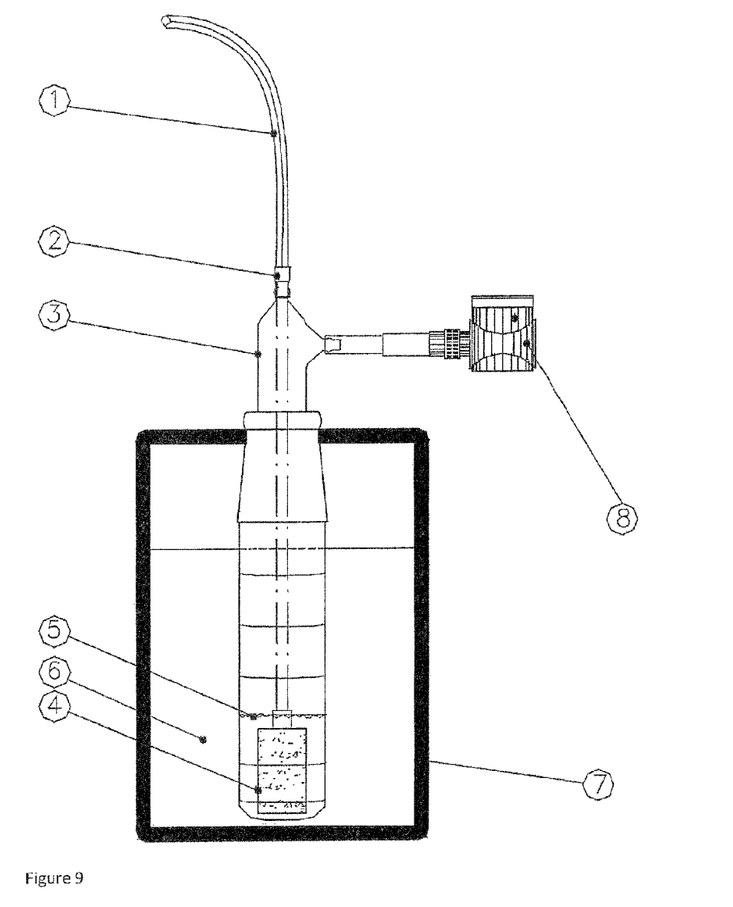
FIG. 9 presents an outline of the device for collecting exhaled air, object of the present invention.
Figure 10:
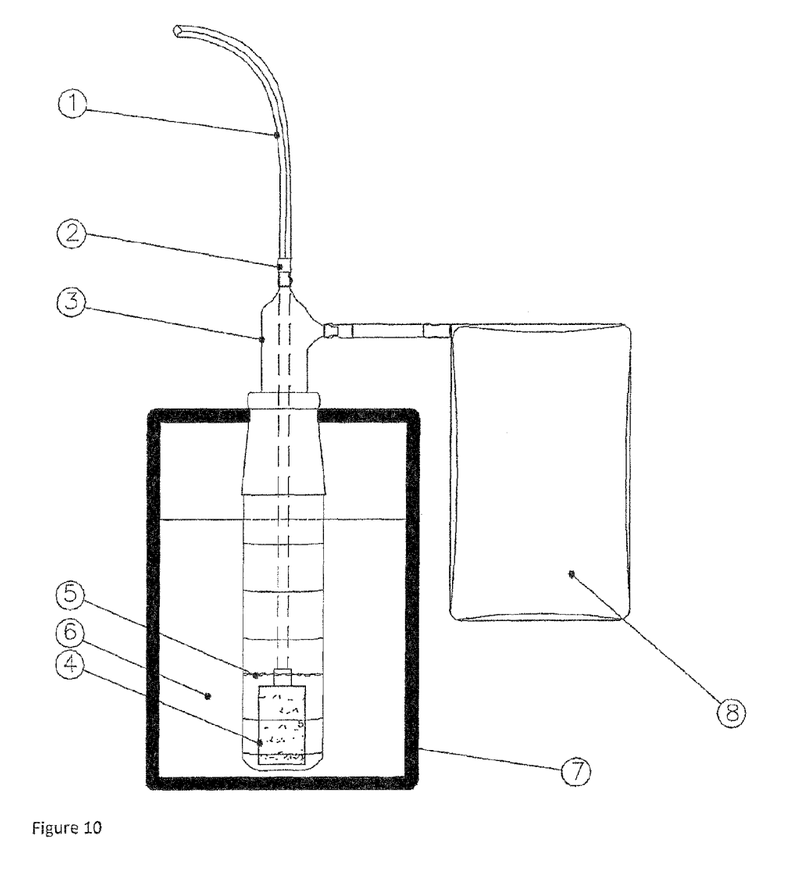
FIG. 10 presents an outline of the device for collecting exhaled air, object of the present invention, a preferred arrangement.

An additional object of the present invention is a device for collecting the biomarker from exhaled air. An embodiment of the device comprises a sample-receiving element (1) arranged to conduct the patient's breath; a connector duct (2) between the element of contact with the patient and a collector element (3); said collector element (3) comprises a diffuser element (4) in its output cavity, said diffuser element being submersed in a fluid element (5), means for extracting and capturing the biomarker; a cooling fluid element (6) indirectly contacting said fluid element (5); an insulating element (7); a volume measuring element (8).

A preferred arrangement of the device for collecting exhaled air comprises a sample-receiving element (1) arranged to conduct the breath of the patient; a connector duct (2) between the element contacting the patient, said receptor element, and a collector element (3); said collector element (3) comprises a diffuser element (4) at its output end, said diffuser element being submersed in a liquid element (5), means for extracting and capturing the biomarker; a cooling element (6) indirectly contacting said fluid element (5); a thermal insulating element (7) and an element for retaining the exhaled air set up to measure and limit the total volume of exhaled air collected (8).

Said diffuser element (4) described previously is made of porous material arranged to guarantee the formation of sufficiently small air bubbles as a means of increasing the contact surface between the volatile compounds contained in the air, especially exposure of the biomarker to the liquid element (5).

The liquid element (5) described previously is a substance having high chemical affinity to acetone selected from the group comprising water, organic compounds and a mixture thereof.

Said preferred arrangement of the device for collecting exhaled air comprises: means for capturing the patient's exhaled air (1); means for extracting and capturing (3) volatile compounds of exhaled air from the patient especially a biomarker of interest; means of diffusing the exhaled air (4) into means for capturing (5) the biomarker; means for indirectly cooling the capturing means (6); means of thermally insulating said device from the external conditions (7) and, means for reading the total volume of exhaled air collected (8).

The means of diffusing the exhaled air (4) described previously is preferably made of porous material set up to guarantee the formation of sufficiently small air bubbles as a means of increasing the contact surface between the volatile compounds contained in the air, especially exposure of the biomarker to the liquid element (5).

The means for extracting and capturing said biomarker (5) have a high chemical affinity with acetone.

An additional object of the present invention is a kit for diagnosing decompensated heart failure comprising a device for collecting exhaled breath air; a fluid for extracting and capturing the biomarker kept cooled; an insulating case for housing the sample containing biomarker and fluid after collection; a biomarker standards kit in different concentrations as a means of calibrating the analytical equipment for guiding the diagnosis based on the analytical technique preferably involving gas chromatography and, a manual as a means of indicating content ranges of the biomarker for diagnosing the severity of decompensated heart failure in view of the content of the biomarker detected.

DETAILED DESCRIPTION

The object of the present invention is a non-invasive method of diagnosing the severity of heart failure. More specifically, the present method is capable of diagnosing decompensated heart failure by the collection, detection and quantification of a specific biomarker. The present invention presents embodiment examples which prove the efficiency of the present non-invasive diagnosis method compared to the currently existing invasive methods. The differentiating factor of the present diagnosis method comprises the diagnosis of the severity of heart failure and by being a non-invasive method, it confers ease of collection and comfort to the patient, and can widely be applied in hospitals.

An additional object of the present invention is a biomarker for diagnosing and prognosticating decompensated HF. The biomarker of said diagnosis method is acetone. This biomarker has never been cited in literature as an indicator of the severity of heart failure, more specifically decompensated heart failure.

To analyze the biomarker for decompensated heart failure various device prototypes have been developed to collect exhaled air to investigate and identify the compounds present in samples from patients obtained in a non-invasive manner. Some prototypes based in literature have not been suitable, for example, that developed by Rosias et al., 2007 cited in the Background of the Invention of the present specification, as it implies in a greater collection time due to the inefficiency in capturing the biomarker, and these devices are not indicated for patients suffering from decompensated HF because they present dyspnea and/or tachypnea, signs of respiratory insufficiency secondary to heart decompensation, rendering unfeasible the conclusion of the collection of exhaled air in a volume suitable for detecting minimum levels of the biomarker. An additional object of the present invention is a device for collecting exhaled air for diagnosing the severity of HF comprising a compound with a high acetone absorption capacity. Said device is portable, easy to handle and fast to collect, being compatible with sufferers of heart decompensation.

For an improved understanding of the present invention, the assays carried out for the embodiment and accreditation of the non-invasive method of diagnosing the severity of heart failure will now be described in detail.

Patients were divided into four distinct groups: control; compensated HF; decompensated HF with congestion and without low output and decompensated HF with low output, congested or not. Group 1 was named Control comprising healthy volunteers without systolic ventricular dysfunction or any acute or chronic disease and without the regular use of medication (sorted by age); Group 2 named CompHF comprising non-diabetic patients suffering from dilated cardiomyopathy of different etiologies with stage C HF, whose symptoms have been stable for at least the last three months, who were being attended as outpatients (consecutive patients that are submitted to the ergospirometric test); Group 3 named CongHF comprising non-diabetic patients suffering from dilated cardiomyopathy of different etiologies with stage C or D HF who present clinical-laboratorial signs of recent decompensation. This group comprises patients with pulmonary and/or systemic congestion, but with preserved perfusion and which, therefore, do not need to use inotropics, whether or not the use of intra-venous vasodilators are necessary (consecutive patients arriving at emergency) and, Group 4 named LOHF comprising non-diabetic patients suffering from dilated cardiomyopathy of different etiologies with decompensated HF in stage C or D who are admitted into the Clinical Emergency Unit and who show signs of low cardiac output (hypoperfusion), congested or not. The use of vasoactive drugs of the inotropic kind is at the discretion of the medical attendant in charge of treating the patient at emergency (consecutive patients arriving at emergency).

The criteria for defining congestion include effort dyspnea; orthopnea; nocturnal paroxistic dyspnea; rest dyspnea; pulmonary stertors; sibilance; lower member edema; jugular stasis; third heart sound and radiological signs of congestion as segment inversion; basal opacity; pleural effusion). The criteria for defining hypoperfusion included hypotension (PAS <80 mmHg); tachycardia; thready pulse; cold extremities; slow capillary refill; nauseas; vomiting; inappetence; oliguria; mental confusion.

Figure 1:
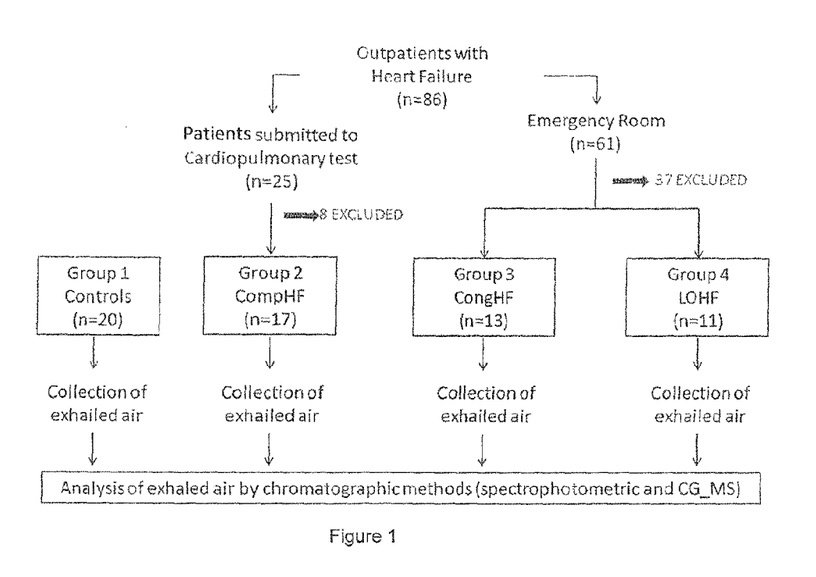
FIG. 1 presents a flowchart of the protocol adopted in the embodiment example of the present invention wherein: CompHF is the denomination for compensated heart failure, CongHF corresponds to congestive heart failure, LOHF corresponds to heart failure with low output, DVA is the name for the vasoactive drug; GC-MS is the name for gas chromatography coupled to mass spectrometry.

For the purposes of the example of embodiment of said non-invasive method of diagnosing the severity of HF, below are the results obtained from a study conducted in a quaternary hospital. The sampling of said example of embodiment comprised 61 patients accompanied at the Heart Failure Outpatients Center and 23 of these patients fulfilled the criteria for inclusion in the study (groups 3—CongHF or 4—LOHF). Among the patients accompanied at the Heart Failure Outpatients Center, 25 stable patients were submitted to the cardiopulmonary test, and of these 17 fulfilled the criteria for inclusion in group 2—CompHF. Twenty patients were selected to participate as control groups, and were sorted by age (average age of 50.0±12, 66% male and 80% white). The reasons for excluding patients from the study were: presence of diabetes mellitus (n=27); absence of the use of carvedilol (n=6); absence of the use of IECA or BRA (n=2); creatinine greater than 2.5 mg/dl (n=7); patient refusal (n=2) and pulmonary infection (n=1). Therefore, 61 patients took part in the assay, of which 20 were from group 1 (control); 17 from group 2 (CompHF); 13 from group 3 (CongHF) and 11 from group 4 (LOHF) as demonstrated in FIG. 1.

For purposes of comparison and proof of the efficiency of the non-invasive diagnosis method proposed by the present invention, each patient was submitted to an invasive method by BNP dosage (B-type atrial natriuretic peptide) described in detail in the Background of the Invention, with collection of blood samples with BNP dosage besides the determination of serum catecholamines, renal function and electrolytes, hemogram, coagulogram, transaminases and lactate, and urine sample to evaluate ketonic bodies and glucose.

The non-invasive diagnosis method comprises the step of collecting samples of exhaled air from patients. This step is preferably carried out by using the collector device, object of the present invention, but without restricting the scope thereof. Said device is suitable for efficiently collecting the acetone, the biomarker of the proposed method.

The step following collection of exhaled air comprises sample transfer to a capped vial and storage of the sample preferably under cooled conditions until the chemical analysis is carried out, if not immediately. In the present example of embodiment, the storage and/or transport temperature was approximately −80° C. but without restricting the scope thereof. This step is called filling step.

The next step corresponds to the analysis of the chemical profile, detection of the acetone and quantification thereof. This step is not the object of protection of the present invention and can be selected in accordance with the availability of analytical equipment such as, for example, gas chromatography, spectrophotometry and others. In the example of embodiment of said detection and quantification of the acetone biomarker, two analytical techniques were selected based on GC-MS and by spectrophotometric method.

As regards the statistical analysis, the Student t-test was used for comparison between proportions for continuous numerical variables and the Chi square distribution or Fisher's exact test was employed used for qualitative variables. The evaluation of the difference between the groups in terms of concentration of acetone was performed by the Kruskal-Wallis non-parametric test, complemented by the Dunn test to show among which groups there were differences. To evaluate the difference between the groups for BNP, a logarithmic transformation was needed, followed by the Bonferroni test. Spearman's rank correlation coefficient was used to describe the relationship between the variables.

Table 1 bears a list of the general characteristics of the patients with HF and the control group and table 2 shows the specific data of the patients with HF divided into three groups.

TABLE 1

General characteristics of patients from the control group and of patients with heart failure

| Characteristics | Control | Patients with HF | p |
|---|---|---|---|
| Age (years) | 50.1 ± 12 | 50 ± 12 | 0.275 |
| Male | 45% | 66% | 0.120 |

HF: Heart failure

TABLE 2

General characteristics of patients with heart failure

| Characteristics | ICCOMP | ICCONG | ICBXDB | p |
|---|---|---|---|---|
| Age (years) | 47.77 ± 11.2 | 56.77 ± 13.8 | 48.72 ± 12.4 | 0.080 |
| Male | 64.7% | 84.2% | 45.5% | 0.152 |
| Etiology | | | | 0.046 |
| Ischemic | 11.8% | 23.1% | 0% | |
| Chagasic | 17.7% | 38.5% | 72.7% | |
| Hypertensive | 29.4% | 7.7% | 9.1% | |
| Idiopathic | 35.3% | 7.7% | 9.1% | |
| Others | 5.9% | 23.1% | 9.1% | |
| NYHA | | | | <0.001 |
| CF 1 | 5.9% | 0% | 0% | |
| CF 2 | 58.8% | 0% | 0% | |
| CF 3 | 35.3% | 69.2% | 27.3% | |
| CF 4 | 0% | 30.8% | 72.7% | |

TABLE 2-continued

General characteristics of patients with heart failure

| Characteristics | ICCOMP | ICCONG | ICBXDB | p |
|---|---|---|---|---|
| Hemodynamic | | | | <0.001 |
| Profile A | 100% | 0% | 0% | |
| Profile B | 0% | 100% | 0% | |
| Profile C | 0% | 0% | 100% | |
| Profile L | 0% | 0% | 0% | |
| Pharmacotherapy | | | | |
| IECA | 76.5% | 100% | 90.9% | 0.154 |
| BRA | 23.5% | 0% | 9.1% | 0.154 |
| Betablocker | 100% | 100% | 100% | 1.0 |
| Spironolactone | 76.5% | 46.2% | 72.7% | 0.221 |
| Hydral/Nitrate | 29.4% | 38.5% | 27.3% | 0.522 |
| Loop Diuretic | 70.6% | 69.2% | 90.9% | 0.428 |
| Thiazide Diuretic | 17.7% | 23.1% | 27.7% | 0.893 |
| Digoxine | 58.8% | 30.8% | 18.2% | 0.156 |
| Comorbidities | | | | |
| HAS | 35.3% | 30.8% | 36.7% | 1.0 |
| Diabetes mellitus | 0% | 0% | 0% | 1.0 |
| Dyslipidemia | 17.7% | 38.5% | 9.1% | 0.223 |
| DPOC | 0% | 0% | 0% | 1.0 |
| IAM | 11.7% | 7.7% | 0% | 0.772 |
| AVC | 5.88% | 23.1% | 9.1% | 0.694 |
| Anemia | 0% | 0% | 9.1% | 0.268 |
| Tobacco smoking | 5.88% | 0% | 9.1% | 0.368 |
| Ethylism | 0% | 0% | 0% | 0.181 |

ICCOMP: compensated heart failure; ICCONG: heart failure with congestion; ICBXDB: heart failure with low output; CF: functional class; IECA: angiotensin-converting enzyme inhibitors II; BRA: angiotensin receptor blockers II; HAS: arterial hypertension; DPOC: chronic obstructive pulmonary disease; IAM: myocardial infarction; AVC: vascular cerebral accident.

Figure 2:
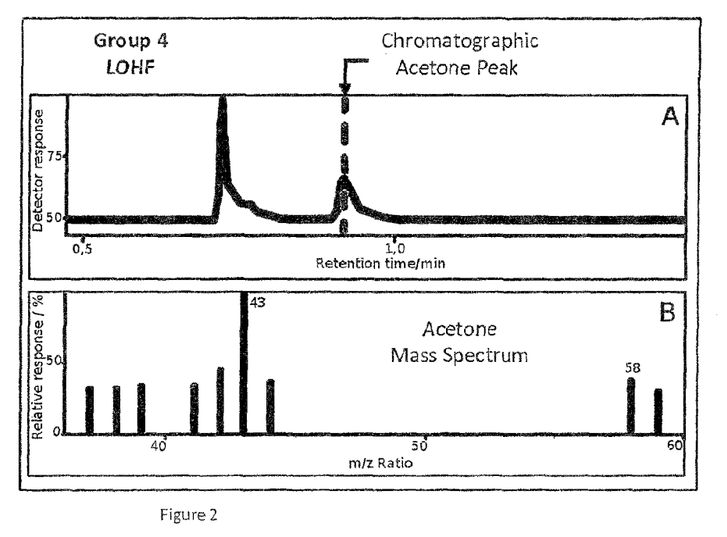
FIG. 2 presents a result of the detection of the biomarker from a sample of the LOHF group in admission, in this example, by gas chromatography coupled to mass spectrometry (GC-MS): (A) the graph represents the separation of the components of the sample in accordance with its greater or lesser affinity with the stationary phase and (B) corresponds to a characteristic acetone mass spectrum, recorded during the elution of the acetone peak in (A).
Figure 3:
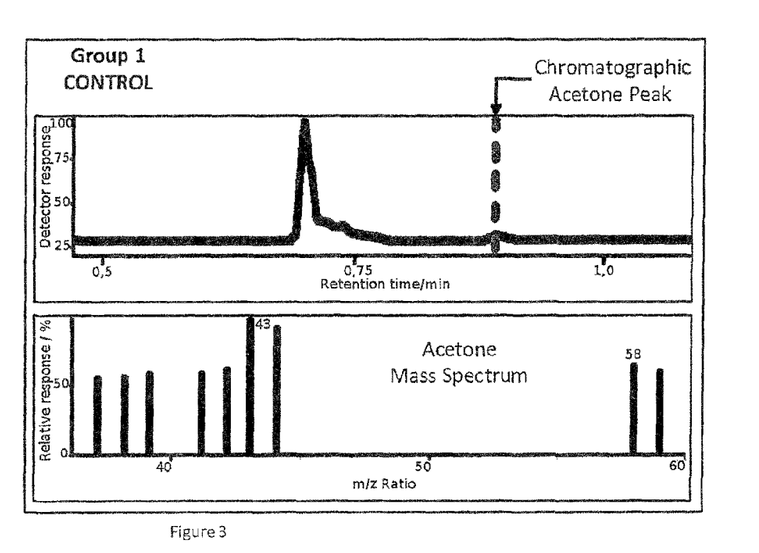
FIG. 3 presents a result of the detection and quantification of a sample of the control group, in this example, through a technique involving gas chromatography coupled to mass spectrometry (GC-MS): (A) the graph represents the separation of the components of the sample in accordance with its greater or lesser affinity with the stationary phase and (B) corresponds to a characteristic acetone mass spectrum, recorded during the elution of the acetone peak in (A).

FIGS. 2 and 3 exemplify the results of the analysis by GC-MS of two patients included in the study: one from the control group (FIG. 2) and one from the group LOHF (FIG. 3). Panel A shows the total ion current (TIC) of the mass spectrometer (current summation at the nine mass/charge ratios listed in the figure), for a chromatogram of each sample and panel B shows the mass spectrum recorded during the elution of the second peak, identified as being acetone.

Figure 4:
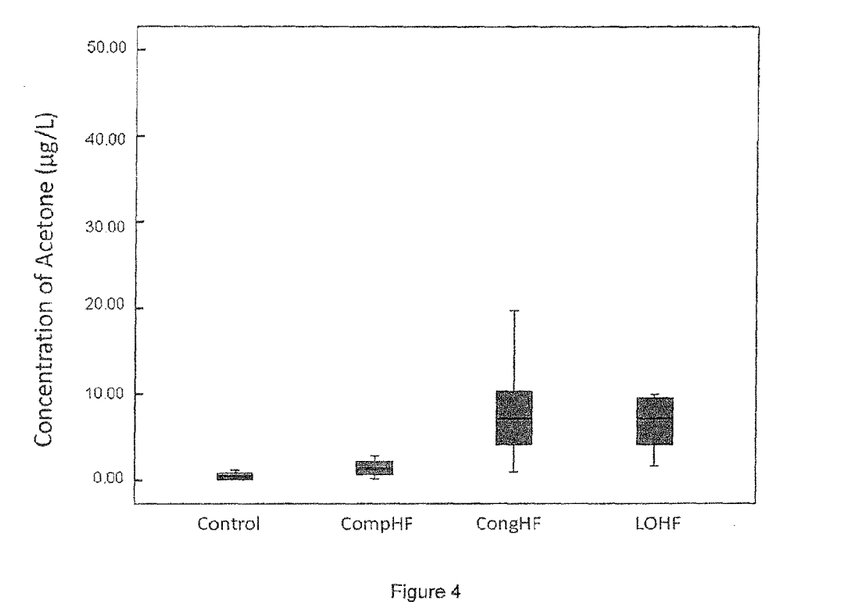
FIG. 4 shows the median concentration of the acetone biomarker, object of the present invention, determined by one of the preferred methods (spectrophotometry), in accordance with the groups evaluated in the embodiment example of said non-invasive diagnosis method comprising an indication of the severity of heart failure with $p<0.001$ among the groups, the groups being named: CompHF—compensated heart failure, CongHF—heart failure with congestion, LOHF—heart failure with low output.
Figure 5:
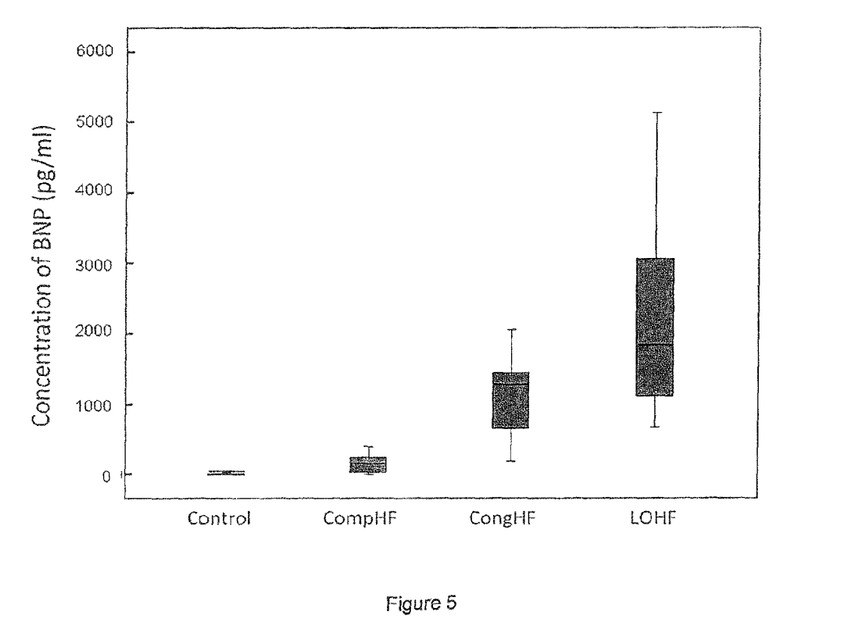
FIG. 5 shows the concentration average of the biomarker BNP, for the effect of comparison with the acetone biomarker, in accordance with the groups evaluate with $p<0.001$ among the groups, the groups being named: CompHF—compensated heart failure, CongHF—heart failure with congestion, LOHF—heart failure with low output.

The statistically significant difference between the groups for the concentration of acetone found (p<0.001) was due to the significant difference between groups LOHF (p<0.05) and CongHF (p<0.05) in relation to group CompHF and between groups LOHF (p<0.05) and CongHF (p<0.05) in relation to the control group (table 3, FIG. 4). There was also a significant difference between the groups for the concentration of BNP (p<0.001), due to the difference between CONTROL and all the other groups (p<0.05) and CompHF and all the other groups (p<0.05) (table 3, FIG. 5). The concentration of serum catecholamines was also different between the groups (p<0.001), due to the difference between CONTROL and all the other groups (p<0.001) and CompHF and all the other groups (p<0.001) (table 3).

TABLE 3

Average and standard deviation of the chemical analyses for the different groups

| Variables | CONTROL | CompHF | CongHF | LOHF | p |
|---|---|---|---|---|---|
| Exhaled acetone (μg/l)* | 0.41 ± 0.39 | 1.40 ± 0.87 | 8.42 ± 5.80 | 10.57 ± 12.4 | <0.001 |
| BNP (pg/ml) | 10.95 ± 8.91 | 185.06 ± 182.74 | 1404 ± 1366 | 2219 ± 1383 | <0.001 |
| Catecholamine (pg/ml) | 266.40 ± 132.44 | 588.53 ± 318.4 | 1048 ± 600.8 | 1242 ± 425.26 | <0.001 |
| Creatinine | 0.84 ± 0.19 | 1.0 ± 0.23 | 1.16 ± 0.31 | 1.37 ± 0.34 | <0.001 |

BNP: B-type atrial natriuretic peptide; ICCOMP: compensated heart failure; ICCONG: heart failure with congestion; ICBXDB: heart failure with low output.
*To express the concentration of acetone in exhaled air in parts per billion in volume (ppbv), multiply concentration by g/L per 422.

Figure 6:
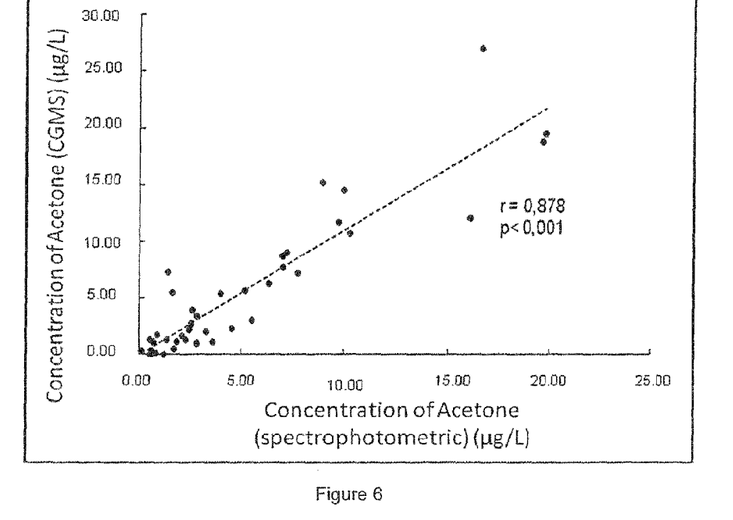
FIG. 6 demonstrates the correlation ($r=0.878$; $p<0.001$) between the concentration of acetone in exhaled air of patients with heart failure, determined by two different quantification techniques, the spectrophotometric and the gas chromatograph with mass spectrometry (CG-MS), emphasizing the fact that the present invention allows an analysis of acetone in patients with heart failure by different techniques and analytic methods.

There was a positive correlation (r=0.878, p<0.001) between the concentrations of acetone determined by different analytical methods (spectrophotometric and by chromatography and mass spectrometry) as illustrated in FIG. 6.

Figure 7:
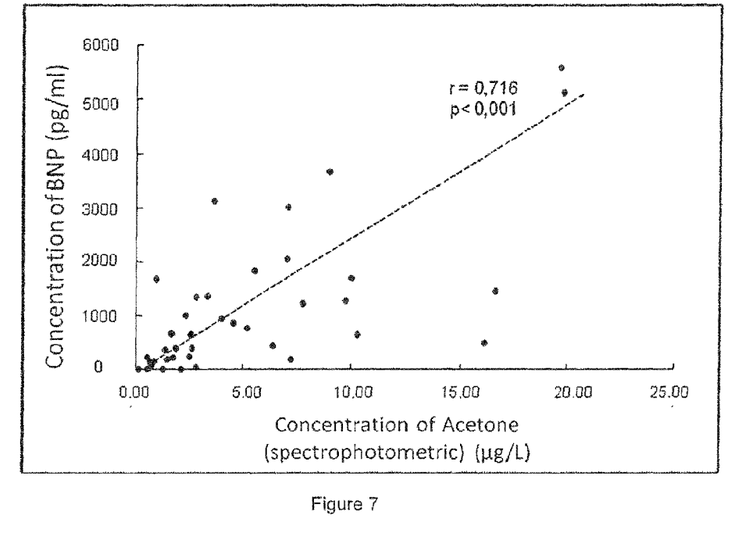
FIG. 7 presents the correlation ($r=0.716$; $p<0.001$) between the concentration of the acetone and BNP biomarkers for patients with heart failure in the different groups, for the purpose of accrediting the non-invasive diagnosis method comprising the use of acetone biomarker as indicative of the severity of heart failure.
Figure 8:
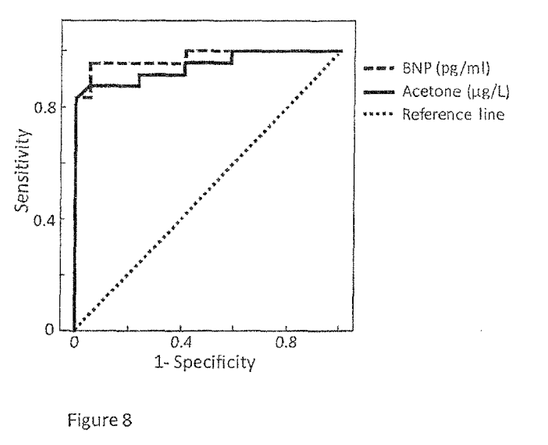
FIG. 8 represents an ROC curve for the concentration of acetone in the population studied showing the degree of sensitivity and specificity of this non-invasive method for diagnosing the severity of heart failure, as well as an ROC curve for the BNP, an already established invasive method for diagnosing heart failure.

There was also a positive correlation between the concentration of acetone and of BNP (r=0.716, p<0.001) as illustrated in FIG. 7.

Determining the concentration of acetone in exhaled air of patients with heart failure as well as BNP, an invasive biomarker of the severity of heart failure already celebrated in literature, provided to be a good forecaster of the severity of the disease, since concentrations greater than 2.6 mcg/L indicated sensitivity of 87.5% and specificity of 88.2% for diagnosing decompensated HF with diagnostic accuracy of 87.8%, regardless of the type of decompensation, be it by congestion or by low output, and this new biomarker has the advantage of being a non-invasive method. Table 4 shows the sensitivity and specificity values for diagnosing chronic HF and severity of HF (decompensated HF) both for exhaled acetone and for BNP. Being non-invasive, the present invention thus compares favorably with the invasive method of the BNP biomarker of severity of heart failure already celebrated in literature.

TABLE 4

Accuracy of the acetone exhaled in the diagnosis of chronic heart failure (cut-off: 0.85 ug/L) and in determining the severity of heart failure (cut-off: 2.6 ug/L) and accuracy of the BNP in the diagnosis of chronic heart failure (cut-off: 20 pg/ml) and in determining the severity of heart failure (cut-off: 420 pg/ml)

| | Sensitivity | Specificity | PPV | NPV | Accuracy |
|---|---|---|---|---|---|
| Exhaled acetone (μg/L) | | | | | |
| Chronic HF diagnosis | 82.9% | 80% | 89.5% | 69.6% | 72% |
| Decompensated HF diagnosis (severity) | 87.5% | 88.2% | 91.3% | 83.3% | 87.8% |
| BNP (pg/ml) | | | | | |
| Chronic HF diagnosis | 90.2% | 90% | 94.9% | 81.8% | 90.2% |
| Decompensated HF diagnosis (severity) | 95.8% | 94.1% | 95.8% | 94.1% | 95.1% |

HF: heart failure; PPV: positive predicted value; NPV: negative predicted value; BNP: B-type atrial natriuretic peptide.

Method of Diagnosing and Prognosticating Decompensated Heart Failure

A non-invasive method of diagnosing heart failure comprising:
(a) analysis of acetone in the exhaled air as a biomarker of heart failure wherein the detection and quantification of the acetone can be made by any suitable technique for direct analysis or after sample collection, which may be selected from a group comprising, but not limited to: chromatography, mass spectrometry, infra-red or ultra-violet-visible spectrophotometry, gas sensors and electronic noses;
(b) indication of the severity of heart failure in accordance with the following ranges:
(b1) acetone concentration with a preferable upper limit of 0.85 mcg/L indicates that the patient does not have a heart failure condition;
(b2) acetone concentration with preferable lower and upper limits of 0.85 up to 2.6 mcg/L indicates compensated heart failure;
(b3) acetone concentration with a preferable lower limit of 2.6 mcg/L indicates decompensated heart failure (heart failure with congestion and/or heart failure with low output).

A non-invasive method of diagnosing heart failure comprising:
(a) means of analyzing acetone in the exhaled air as a biomarker of heart failure wherein the detection and quantification of the acetone can be made by any suitable technique for direct analysis or after sample collection, which may be selected from a group comprising, but not limited to: chromatography, mass spectrometry, infra-red or ultra-violet-visible spectrophotometry, gas sensors and electronic noses;
(b) means of indicating of the severity of heart failure in accordance with the following ranges:
(b1) acetone concentration with a preferable upper limit of 0.85 mcg/L indicates that the patient does not have a heart failure condition;
(b2) acetone concentration with preferable lower and upper limits of 0.85 up to 2.6 mcg/L indicates compensated heart failure;
(b3) acetone concentration with a preferable lower limit of 2.6 mcg/L indicates decompensated heart failure (heart failure with congestion and/or heart failure with low output).

An additional object of the present invention is a non-invasive method of prognosticating heart failure comprising:
(a) collection of a sample of exhaled air in a device that extracts one or more biomarkers from gaseous phase to a liquid phase comprising pure water, organic substances with high acetone affinity, chemical reagents or mixtures of substances that increase the retention efficiency of the biomarker of interest.
(b) detection and quantification of the acetone biomarker in the sample of the exhaled air wherein the analytical technique can be selected from a group comprising, but not limited to: chromatography, mass spectrometry, infra-red or ultra-violet-visible spectrophotometry, gas sensors and electronic noses; and
(c) indication of the prognosis of the patient suffering from decompensated heart failure comprising the following ranges:
(c1) acetone concentration with a preferable upper limit of 0.85 mcg/L indicates that the patient does not have a heart failure condition;

(c2) acetone concentration with preferable lower and upper limits of 0.85 up to 2.6 mcg/L indicates compensated heart failure;

(c3) acetone concentration with a preferable lower limit of 2.6 mcg/L indicates decompensated heart failure (heart failure with congestion and/or heart failure with low output).

An additional object of the present invention is a non-invasive method of prognosticating heart failure comprising:

(a) means of collecting a sample of exhaled air in a device that extracts one or more biomarkers from gaseous phase to a liquid phase comprising pure water, organic substances with high acetone affinity, chemical reagents or mixtures of substances that increase the retention efficiency of the biomarker of interest.

(b) means of detecting and quantificating the acetone biomarker in the sample of the exhaled air wherein the analytical technique can be selected from a group comprising, but not limited to: chromatography, mass spectrometry, infrared or ultra-violet-visible spectrophotometry, gas sensors and electronic noses; and (c) means of indicating of the prognosis of the patient suffering from decompensated heart failure comprising the following ranges:

(c1) acetone concentration with a preferable upper limit of 0.85 mcg/L indicates that the patient does not have a heart failure condition;

(c2) acetone concentration with preferable lower and upper limits of 0.85 up to 2.6 mcg/L indicates compensated heart failure;

(c3) acetone concentration with a preferable lower limit of 2.6 mcg/L indicates decompensated heart failure (heart failure with congestion and/or heart failure with low output).

In the collection step (a) of said method, a substance having affinity with biomarker is preferably but not limited to water.

In the collection step (a) of said method, a chemical reagent for the biomarker is preferably but not limited to 2,4-dinitrophenylhydrazine (DNPH).

In the collection step (a) of said method, a substance having affinity with the biomarker is a mixture of water and 2,4-dinitrophenylhydrazine (DNPH).

Said collection step (a) is preferably at a temperature of between −10 and 15° C. preferably between −5 e 5° C. The temperature can be maintained, for example, through thermal gels, ice bath or metal cylinder inside a thermal insulator.

Said collection step (a) is conducted by exhaling air through the mouth into the device preferably up to a volume of 7 liters, limited by the volume defining bag.

Said collection step (a) is capable of retaining at least 0.5 μg/L of acetone in the sample of the exhaled air.

According to the method described previously, between steps (a) and (b), there is a storage step of the collected sample at a temperature of between −90 and −0° C., preferably between −80 and −20° C.

The use of the acetone biomarker is now the first exhaled biomarker for heart failure, its dosage being made by non-invasive diagnosis method and may be related to higher severity of the disease, since the highest values were found in patients admitted to emergency with more serious clinical signs. Thus in this present embodiment, the non-invasive diagnosis method proposed predicts the severity of heart failure.

Method of detecting, identifying and quantifying the biomarker, in addition to its equipment are known in the state of the art and, therefore, for full disclosure of the present invention, but without restricting the scope, the method of analysis, detection and quantification of the acetone by other techniques and devices is presented below.

To identify the most significant chemicals added to exhaled air by patients with heart failure, in the present example of embodiment of said invention, but without restricting the scope thereof, the technique known as GC-MS was used, a combination of gas chromatography (GC) with mass spectrometry (MS), given its potential for multiple-constituent separation, identification and semi-quantitative determination in the samples, with high sensitivity and selectivity. Gas chromatography (GC) is a physical separation method in which the sample is injected into a column, in this particular case, capillary with a suitably immobilized stationary phase on its inner wall. The separation of the components of the sample is, as a general rule, in accordance with its greater or lesser affinity with the stationary phase or the mobile gaseous phase. Due to its simplicity, sensitivity and effectiveness to separate the components in the mixture, gas chromatography is one of the most important techniques in chemical analysis. Mass spectrometry (MS) is an analytical technique of separating and detecting ions according to its mass-charge ratio by diverting its trajectory into a chamber under vacuum by applying electrical fields, in combination or not with magnetic fields. The molecules of the sample need to be ionized before introduction into the spectrometer, and the fragmentation of molecules also usually occurs in this process. Based on the mass-charge ratio of the ions detected, it is generally possible to identify the molecules of origin, provided that the mixtures are not complex, in which case prior chromatographic separation is necessary. By these two methods, it is possible to detect the presence of acetone in the samples analyzed.

For the exact quantification of the acetone biomarker, a spectrophotometric method was selected, but without restricting the scope, to measure the absorption of light in the wavelength having greater absorptiveness of the colored product of the reaction between acetone and salicylaldehyde (spectrophotometric). The method was adjusted so that it was only necessary to add 500 μL of colorimetric reagent (salicylaldehyde solution in an alkaline medium) to 500 μL of the sample, wait for the reaction to develop and measure the absorbance in a cuvette placed in the spectrophotometer, it being directly proportional to the concentration of acetone in the sample. Calibration is carried out by submitting aqueous solutions with a known concentration of acetone to the same procedure. The results were converted into concentration of the acetone biomarker in the exhaled air.

Device

In the present invention the device for collecting exhaled air involves extraction by dissolution of the acetone exhaled into a fluid. Some factors influence the efficiency of the collection: size and porosity of said diffuser described previously, thin pores generate smaller air bubbles favoring the dissolution of the acetone of said fluid; level and temperature of the fluid and solubility of the acetone in said fluid. These factors allow greater contact, mixture and increased solubility of the biomarker, implying in greater sensitivity of the non-invasive diagnosis method.

FIGS. 9 and 10 schematically represent examples of arrangements of said device, but without restricting the scope of their shapes and sizes.

An additional object of the present invention is a device for collecting exhaled air which comprises: means for capturing the exhaled air from the patient (1); means for extracting and capturing (3) volatile compound(s) from the exhaled air of the patient especially a biomarker of interest; means of diffusing the exhaled air (4) into means for capturing (5) a biomarker; means for indirectly cooling (6) the capturing means (5); means of insulating said device from the external conditions (7) and, means for reading the total volume of exhaled air collected (8).

The means of diffusing the exhaled air described previously (4) are preferably made of porous material or fine holes arranged to guarantee the formation of sufficiently small air bubbles as a means of increasing the contact surface between the volatile compounds contained in the air, especially the exposure of the biomarker and capturing means (5).

The means for extracting and capturing said biomarker (5) have a high chemical affinity with acetone.

Said device for collecting exhaled air comprises: a sample-receiving element (1) arranged to conduct the patient's breath; a connector duct (2) between the element of contact with the patient and a collector element (3); said collector element (3) comprises a diffuser element (4) in its output cavity, said diffuser element being submersed in a liquid element (5), means for extracting and capturing the biomarker; contained in a recipient, preferably made of glass or plastic; a liquid, solid (ice), mixed or thermoelectric (6) cooling element in contact with the outer walls of said recipient (5); a thermal insulating element (7); a volume measuring element (8).

A preferred arrangement of said device for collecting exhaled air comprises: a sample-receiving element (1) arranged to conduct the patient's breath; a connector duct (2) between the element of contact with the patient and a collector element (3); said collector element (3) comprises a diffuser element (4) in its output cavity, said diffuser element being submersed in a fluid element (5), means for extracting and capturing the biomarker; a cooling fluid element (6) indirectly contacting said fluid element (5); an insulating element (7) and, an element for retaining the exhaled air set up to measure the total volume of exhaled air collected (8).

Said diffuser element (4) described previously is made of porous material set up to guarantee the formation of sufficiently small air bubbles as a means of increasing the contact surface between the volatile compounds contained in the air, especially the exposure of the biomarker to the fluid element (5).

The liquid element (5) described previously is a substance having high chemical affinity with acetone selected from the group comprising water, organic compounds and a mixture thereof.

In the embodiment example of said invention, the fluid (5) comprises a volume preferably of 5 mL and a temperature lower than ambient temperature as a means of rising between 2 and 4 times Henry's constant value allowing a more efficient collection of the biomarker.

Said diffuser element (4) as a means of increasing the contact surface of the gas/liquid and can be selected from the group of porous materials comprising sintered glass or a polymeric tube with various micro-perforations in the closed end region, preferably disposable.

The fluid (5), a means to increase the capture efficiency of the biomarker, comprises a composition selected from the group of water or other compounds, with or without addition of chemical reagents.

Use of Biomarker to Diagnose the Severity of Decompensated Heart Failure

Use of acetone as biomarker for diagnosing the severity of heart failure according to its concentration levels.

Use of acetone as biomarker for prognosticating intrahospital mortality.

Diagnosis Kit

An additional object of the present invention is a kit for diagnosing decompensated heart failure comprising a device for collecting exhaled breath air; a fluid for extracting and capturing the biomarker kept cooled; an insulating case for housing the sample containing biomarker and fluid after collection; a biomarker standards kit in different concentrations as a means of calibrating the analytical equipment for guiding the diagnosis based on the analytical technique preferably involving gas chromatography, and a manual as a means of indicating content ranges of the biomarker for diagnosing the severity of decompensated heart failure in view of the content of the biomarker detected.

That which is claimed:

1. A non-invasive method of diagnosing heat failure, comprising:
    (a) collecting a sample of exhaled air using a capture device comprising:
        (i) means for capturing the exhaled air directly from a patient;
        (ii) means for extracting and capturing volatile compound(s) from the captured exhaled air of the patient especially a biomarker of interest;
        (iii) means of diffusing the captured exhaled air into means for capturing a biomarker;
        (iv) means for indirectly cooling the capturing means;
        (v) means of insulating said capture device from external conditions; and,
        (vi) means for reading total volume of exhaled air collected;
    b) analyzing, using a processor, the sample of captured exhaled air for acetone as a biomarker of heart failure, wherein the detection and quantification of the acetone can be made by any suitable technique selected from the group consisting of chromatography, mass spectrometry, infra-red or ultra-violet spectrophotometry, gas sensors and electronic noses; and
    c) indicating, using the processor, the severity of heart failure in accordance with the following ranges of acetone in the sample of exhaled air:
        (i) acetone concentration with an upper limit of 0.85 mcg/L indicates that the patient does not have a heart failure condition;
        (ii) acetone concentration with lower and upper limits of 0.85 mcg/L and 2.6 mcg/L indicates compensated heart failure; and
        (iii) acetone concentration with a lower limit of 2.6 mcg/L indicates decompensated heart failure, characterized by heart failure with congestion and/or heart failure with low output.

2. A non-invasive method of prognosticating heat failure, comprising:
    (a) collecting a sample of exhaled air using a capture device comprising:
        (i) means for capturing the exhaled air directly from a patient;
        (ii) means for extracting and capturing volatile compound(s) from the captured exhaled air of the patient especially a biomarker of interest;
        (iii) means of diffusing the captured exhaled air into means for capturing a biomarker;
        (iv) means for indirectly cooling the capturing means;
        (v) means of insulating said capture device from external conditions; and,
        (vi) means for reading total volume of exhaled air collected;
    b) analyzing, using a processor, the sample of captured exhaled air for acetone as a biomarker of heart failure, wherein the detection and quantification of the acetone can be made by any suitable technique selected from the group consisting of chromatography, mass spectrometry, infra-red or ultra-violet spectrophotometry, gas sensors and electronic noses; and
    c) indicating, using the processor, the prognosis of the patient suffering from decompensated heart failure in accordance with the following ranges of acetone in the sample of exhaled air:

(i) acetone concentration with an upper limit of 0.85 mcg/L indicates that the patient does not have a heart failure condition;
(ii) acetone concentration with lower and upper limits of 0.85 mcg/L and 2.6 mcg/L indicates compensated heart failure; and
(iii) acetone concentration with a lower limit of 2.6 mcg/L indicates decompensated heart failure, characterized by heart failure with congestion and/or heart failure with low output.

3. The method according to claim 2, wherein the collection step (a) is conducted at a temperature of between −10° C. and 15° C., or between −5° C. and 5° C.

4. The method according to claim 2, wherein the collection step (a) is conducted by the patient blowing air through the mouth into the device, and with an air volume at least 7 liters.

5. The method according to claim 2, wherein the collection step (a) method according is capable of retaining at least 0.2 μg/L of acetone in the sample of exhaled air.

6. The method according to claim 2, further comprising a filling and storage step of the sample of exhaled air between steps (a) and (b), said filling and storage step occurring at a temperature between −90° C. and −0° C., or between −80° C. and −20° C.

7. The method according to claim 1, wherein collection step (a) is conducted at a temperature of between −10° C. and 15° C., or between −5° C. and 5° C.

8. The method according to claim 1, wherein the collection step (a) is conducted by a patient blowing air through the mouth into the device, and with an air volume of at least 7 liters.

9. The method according to claim 1, further comprising a filling and storage step of the sample of exhaled air between steps (a) and (b), said filling and storage step occurring at a temperature between −90° C. and 0° C., or between −80° C. and −20° C.

10. The method according to claim 1, wherein the device comprises:
    (i) a sample-receiving element (1) arranged to conduct the patient's breath;
    (ii) a connector duct (2) between the element of contact with the patient and a collector element (3), wherein said collector element (3) comprises a diffuser element (4) in its output cavity, said diffuser element being submersed in a fluid element (5), means for extracting and capturing the biomarker;
    (iii) a cooling fluid element (6) indirectly contacting said fluid element (5);
    (iv) an insulating element (7); and
    (v) an element for retaining the exhaled air set up to measure the total volume of exhaled air collected (9).

11. The method according to claim 10, wherein said diffuser element (4) is made of porous material arranged to increase a contact surface between the volatile compounds contained in the air.

12. The method according to claim 10, wherein said diffuser element (4) is preferably sintered glass or porous polymer.

13. The method according to claim 10, wherein said fluid element (5) is a substance having high chemical affinity with acetone selected from the group consisting of water, organic compounds, and a mixture thereof.

14. The method according to claim 13, wherein the fluid element (5) is water.

15. The method according to claim 13, wherein the fluid element (5) is a mixture of water and 2,4-dinitrophenylhydrazine (DNPH).

16. The method according to claim 10, wherein the fluid element (5) occupies a volume of 5 mL inside the collector element (3) and behind the diffuser element (4) and a temperature lower than ambient temperature as a means of rising between 2 and 4 times Henry's constant value.

17. The method according to claim 10, wherein the device further comprises an air volume reader (8) or delimiter (8).

18. The method according to claim 2, wherein the device comprises:
    (i) a sample-receiving element (1) arranged to conduct the patient's breath;
    (ii) a connector duct (2) between an element of contact with the patient and a collector element (3), wherein said collector element (3) comprises a diffuser element (4) in its output cavity, said diffuser element being submersed in a fluid element (5), means for extracting and capturing the biomarker;
    (iii) a cooling fluid element (6) indirectly contacting said fluid element (5);
    (iv) an insulating element (7); and
    (v) an element for retaining the exhaled air set up to measure the total volume of exhaled air collected (9).

19. The method according to claim 18, wherein said diffuser element (4) is made of porous material arranged to increase a contact surface between the volatile compounds contained in the air.

20. The method according to claim 18, wherein said diffuser element (4) is preferably sintered glass or porous polymer.

21. The method according to claim 18, wherein said fluid element (5) is a substance having high chemical affinity with acetone selected from the group consisting of water, organic compounds, and a mixture thereof.

22. The method according to claim 21, wherein the fluid element (5) is water.

23. The method according to claim 21, wherein the fluid element (5) is a mixture of water and 2,4-dinitrophenylhydrazine (DNPH).

24. The method according to claim 18, wherein the fluid element (5) occupies a volume of 5 mL inside the collector element (3) and behind the diffuser element (4) and a temperature lower than ambient temperature as a means of rising between 2 and 4 times Henry's constant value.

25. The method according to claim 18, wherein the device further comprises an air volume reader (8) or delimiter (8).

* * * * *